United States Patent
Lauritsch et al.

(10) Patent No.: US 7,406,347 B2
(45) Date of Patent: Jul. 29, 2008

(54) DEVICE FOR MAKING VISIBLE A PATHOLOGICAL CHANGE IN A PART OF THE BODY LABELED WITH A FLUORESCENT DYE

(75) Inventors: Günter Lauritsch, Erlangen (DE); Marcus Pfister, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/330,575

(22) Filed: Jan. 12, 2006

(65) Prior Publication Data

US 2006/0167357 A1    Jul. 27, 2006

(30) Foreign Application Priority Data

Jan. 13, 2005    (DE)    ........................ 10 2005 001 682

(51) Int. Cl.
*A61B 6/00* (2006.01)
(52) U.S. Cl. .................. 600/431; 600/473; 600/476
(58) Field of Classification Search .................. 600/407, 600/431, 473, 476, 310, 312
See application file for complete search history.

(56) References Cited

U.S. PATENT DOCUMENTS

| | | | |
|---|---|---|---|
| 6,021,344 A * | 2/2000 | Lui et al. ..................... | 600/476 |
| 6,032,070 A * | 2/2000 | Flock et al. .................. | 600/473 |
| 6,230,046 B1 * | 5/2001 | Crane et al. .................. | 600/476 |
| 6,439,715 B2 | 8/2002 | Burckhardt | |
| 7,006,861 B2 * | 2/2006 | Flock et al. .................. | 600/473 |
| 2002/0016533 A1 * | 2/2002 | Marchitto et al. ........... | 600/310 |
| 2003/0018271 A1 * | 1/2003 | Kimble ........................ | 600/473 |
| 2005/0033145 A1 * | 2/2005 | Graham et al. .............. | 600/407 |

FOREIGN PATENT DOCUMENTS

DE    103 39 784 A1    3/2004

OTHER PUBLICATIONS

A. Wall, C. Bremer, L. Matuszewski, T. Häupl, M. Pfister, W. Heindel, "New Multichannel Fluorescence Reflectance Imaging System for Small Animal Applications", Proceedings of the ECR, 2003, p. 1, Vienna.

Umar Mahmood, Ching-Hsuan Tung, Alexei Bogdanov, Ralph Weissleder, Near-Infrared Optical Imaging of Protease Activity for Tumor Detection, Radiology, Dec. 1999, pp. 866-870, vol. 213, No. 3.

* cited by examiner

*Primary Examiner*—Brian L. Casler
*Assistant Examiner*—James Kish

(57) ABSTRACT

The invention relates to a device for making visible a pathological change in a part of a patient's body labeled with a fluorescent dye, the device having: a first selectable light source (11, 17), which emits light in the excitation wavelength range of the fluorescent dye, in order to trigger the emission of light in the emission wavelength range of the fluorescent dye, a second selectable light source, which emits visible light outside the emission wavelength of the fluorescent dye, and a means for selectively switching the first and the second light source on and off.

12 Claims, 3 Drawing Sheets

DEVICE FOR MAKING VISIBLE A PATHOLOGICAL CHANGE IN A PART OF THE BODY LABELED WITH A FLUORESCENT DYE

CROSS REFERENCE TO RELATED APPLICATIONS

This application claims priority to the German application No. 10 2005 001 682.0, filed Jan. 13, 2005 which is incorporated by reference herein in its entirety.

FIELD OF INVENTION

The invention relates to a device for making visible a pathological change in a part of a patient's body labeled with a fluorescent dye.

BACKGROUND OF INVENTION

Fluorescent metabolic markers which accumulate in certain pathologically altered regions of the body are known, for example, in the case of tumors, inflammations or other foci of infection. In addition, fluorescent metabolic markers are known which can be distributed everywhere in the body but which are activated only in certain body regions, by for example, tumor-specific enzyme activities. For this purpose, the metabolic marker is administered to the patient in the form of a fluorescent dye and this fluorescent dye is administered into the bloodstream, for example.

SUMMARY OF INVENTION

Fluorescent dyes have an excitation wavelength and an emission wavelength that differs therefrom. When the fluorescent dye is irradiated with light at the excitation wavelength, emission ensues at the emission wavelength. Since this process involves a loss of energy, emission generally occurs at a higher wavelength than excitation.

The invention addresses the problem of providing a device with which pathological changes in a part of the body labeled with a fluorescent dye can easily be identified.

To solve the above problem, a device of the type mentioned in the opening paragraph and having the following features is provided: a first selectable light source, which emits light in the excitation wavelength range of the fluorescent dye, in order to trigger the emission of light in the emission wavelength range of the fluorescent dye, a second selectable light source, which emits visible light outside the emission wavelength of the fluorescent dye, and a means for selectively switching on and off the first and the second light source.

By means of the invention a simply designed device is created which makes it possible to identify fluorescently labeled parts of the body. The device according to the invention is suitable in particular for use in operations; the limits of tumors, for example, may be detected by the physician treating the patient during the resection of fluorescently labeled tumors. Similarly, fluorescently labeled skin cancer can be made visible.

According to the invention, the device comprises the first selectable light source, which emits light in the excitation wavelength range of the fluorescent dye. This light source triggers the emission of light by the fluorescent dye in the region of the pathologically altered part of the body. Since the excitation light and the emitted light have different wavelengths, they can easily be kept apart. When the first selectable light source is switched on, the fluorescent image is visible to the physician treating the patient.

The device according to the invention further comprises the second selectable light source, which emits visible light outside the emission wavelength of the fluorescent dye. The second light source illuminates the area for investigation or operation, such that the physician treating the patient can see the anatomical structures and, where necessary, the instruments used in an operation. The image generated by the second light source is referred to as the native image.

According to the invention the device comprises a means for switching the first and the second light source on and off selectively, such that either the fluorescent image or the native image is produced.

Preferably, the light sources can be selected by the means in such a way that the impression of a superimposed image is created. In this way, the relevant image information for the native image and for the fluorescent image may be combined in an advantageous manner to form a superimposed image. Firstly, the physician can detect a pathological change since this body area is optically detectable by means of the fluorescent dye, and in particular, the spatial extent of the pathologically altered region of the body can be detected. In addition, the area being operated on and, where necessary, the instruments used are visible. Since the pathologically altered regions of the body and the three-dimensional extent thereof can be detected exactly, the removal thereof in the context of an operation can be carried out with particular precision.

A further improvement of the device can be achieved with a filter which filters out any parts of the ambient light or existing light that may be present in the emission wavelength range. This prevents components of the ambient light that are of the wavelength of the emitted light from making the detection of the pathologically altered region more difficult. Preferably, the filter can be turned on and off, as a result of which the properties of the filter are adjustable and selectable. The use of the filter is particularly helpful at times when the second light source is switched on. Accordingly provision can be made for it to be possible to turn the filter on and off synchronously with the second light source. In this case, components of the ambient light in the emission wavelength range can be filtered out by the filter when the second light source is switched on, thus ensuring that the visible emitted light is actually triggered by the emission of the fluorescent dye.

In a further embodiment of the invention provision can be made for the frequency at which the light source is turned on and off to be adjustable. If the first and the second light source are each turned on and off alternately at high frequency, the human eye is then unable to distinguish between the two images that have been generated in different ways, that is, the fluorescent image and the native image, with the result that the impression of a superimposed merged image is created.

In order to make it possible to use the device according to the invention in a simple manner, provision can be made for the filter to be made of light-permeable glass, through which the part of the body that is to be examined can be viewed. In this way, it is possible to filter out any unwanted components of the ambient light or existing light which may be present and which could otherwise lead to distortion or impairment of the fluorescent image.

In order to make the use of the device even simpler, provision can be made for it to be configured as a hand-held device. The device can have a handle and preferably a transparent filter surface connected thereto.

According to an alternative embodiment of the invention, the device can be designed to be worn on the side of or on top of the head, as a pair of glasses for example, one or both lenses being configured as filters. It is also possible for the device to be of a detachable design, by securing it to a headband.

The device according to the invention can further comprise a light screen to screen off existing light or ambient light, so that no unwanted components of the light strike the part of the body that is to be examined.

BRIEF DESCRIPTION OF THE DRAWINGS

Further advantages and details of the invention are explained in the embodiments with the aid of the drawings. The drawings are in diagram form and show.

DETAILED DESCRIPTION OF INVENTION

Figure 1:
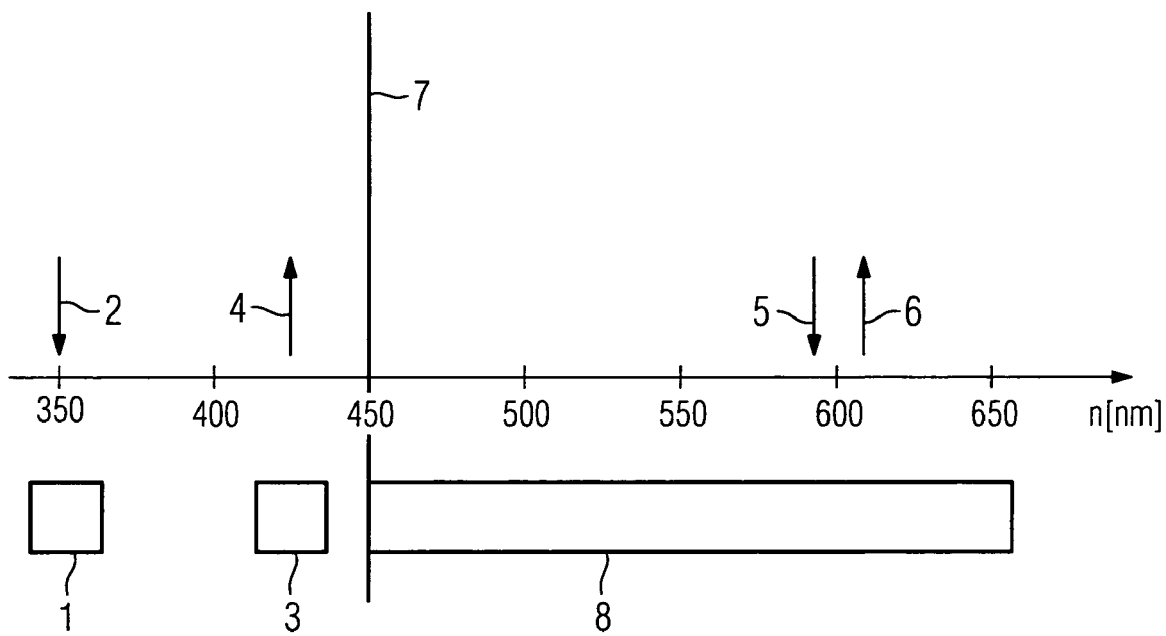
FIG. 1 a diagram, in which the reflected light, the fluorescent light and the existing light are shown across the wavelength.

FIG. 1 is a diagram showing the various components of light which play a part in the realization of the invention. The horizontal axis shows the wavelength in nanometers. Under this axis, the components of light are shown in bar sections.

In the embodiment shown, the point of departure is a fluorescent dye with an excitation frequency 1 of about 350 nm. The downwards-pointing arrow 2 shows that the light hits the part of the body under investigation with the excitation frequency 1. This fluorescent dye has an emission wavelength 3, which is shown by the upwards-pointing arrow 4. This means that during irradiation at the excitation wavelength 1, emission ensues at the emission wavelength 3. The fluorescent dye is a metabolic marker, which has the characteristic of accumulating in pathologically altered parts of the body, e.g. where there is a tumor, an inflammation or suchlike. It is also possible for the fluorescent metabolic marker to be distributed all over the body, but for the activation thereof only to be possible, for example, as a result of tumor-specific enzyme activities in certain parts of the body. The detection of a part of the body that has been fluorescently labeled in this way is achieved by irradiating this part of the body with light at the specific excitation wavelength of the fluorescent dye and by detecting the light emitted in the respective emission wavelength of the fluorescent dye. Studies have shown that the intensity of fluorescence is correlated to the aggressivity of the respective tumor. The device according to the invention allows in the first instance investigations of areas close to the surface or investigations of an open body to be carried out, that is, intra-operative applications in particular. Examples thereof are the detection of fluorescently labeled skin cancer and of the limits of tumors, for example, during the resection of fluorescently labeled tumors.

As shown in FIG. 1, the physician treating the patient can see the fluorescent image when the part of the body under investigation is irradiated at the excitation wavelength 1 and emits light at the emission wavelength 3. In the context of a surgical intervention it also necessary, however, for the physician treating the patient to be able to see the surrounding area and where necessary, his instruments. For this reason, the device can be switch-selected, such that the native image, that is the natural image, becomes visible. To achieve this, the light source, with which the fluorescent dye is excited, is turned off and at the same time, the other light source, which emits visible light, at a wavelength of 600 nm for example, is turned on, as is shown in FIG. 1 by the downwards-pointing arrow 5. Accordingly, incoming light is reflected at the same wavelength, as shown by the arrow 6, with the result that the native image, which is also referred to as the reflected image, is visible. The light from the second light source is within the existing light spectrum 8.

In order to achieve separation between the fluorescent image and the reflected image, a filter 7, shown in diagram form in FIG. 1, may optionally be used. This filter has the property of filtering out any components of the existing light spectrum 8 that may be present in the emission wavelength range. In the embodiment shown, the filter 7 filters out those light components that have a wavelength shorter than 450 nm. Alternatively a band pass filter, which filters out only a specific range in the spectrum, could be used.

Figure 2:
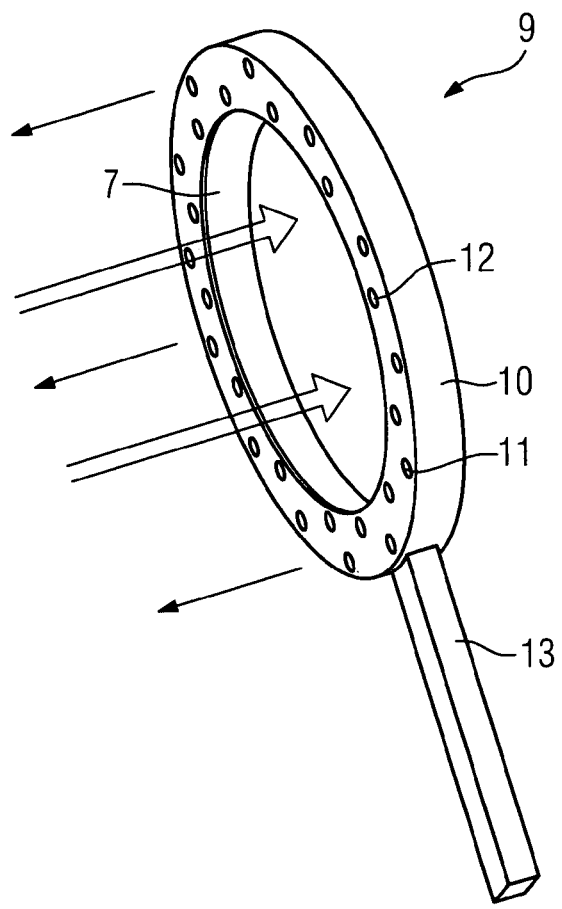
FIG. 2 a first embodiment of a device according to the invention.

FIG. 2 shows a first embodiment of the invention. The device 9 is configured as a hand-held device and consists essentially of a ring 10, which serves as a mounting for the filter 7, and also a handle 13. On the underside of the ring 10, light-emitting diodes 11, 12 are arranged around the circumference as first and second light sources. The light-emitting diodes 11 that form the outer ring emit light at the excitation wavelength of the fluorescent dye used; in the present embodiment the excitation wavelength is 350 nm. The light-emitting diodes 12 forming the inner ring emit light in the visible range; in the embodiment shown the wavelength is 600 nm.

The light-emitting diodes 11, 12, each set of which is arranged in a circle, can be switched on and off by a switching means. Said switching means can either be integrated into the body of the ring 10 or into the handle 13. Furthermore, an energy source is provided therein, such as a battery or an accumulator, for example. The switching means switches at high frequency between the light-emitting diodes 11 and 12. When the light-emitting diodes 11 are turned on, the fluorescent dye is irradiated at the excitation wavelength. The filter 7 can be switched on and off in a similar way to the light-emitting diodes. Only if the filter 7 is switched on does it filter out of the existing light the wavelength range below 450 nm. The filter 7 is therefore turned on at the same time as the light-emitting diodes 12 which emit light at a wavelength of about 600 nm. The filter ensures that any components of the existing light that may be present that have a wavelength under 450 nm are filtered out, and these light components cannot therefore be confused in error with the emission light emitted by the fluorescent dye. Thus the emission light is visible if the light-emitting diodes 11 are switched on. If the light-emitting diodes 12 are switched on, the native image is visible in the existing light spectrum. If a changeover is effected quickly enough between these two states, the human eye can no longer separate these states from each other, with the result that a common merged image is generated. In this superimposed image, any pathological change that may be present can be detected as a spot that glows more intensely within the surrounding tissue. The selectable filter 7 can also be configured as a tunable filter (Liquid Crystal Tunable filter, LCTF). In such filters, the filter properties can be changed by means of electric signals. In the simplest instance, the LCTF can be switched back and forth between two states, either filtering out wavelengths in the emission wavelength range of the fluorescent dye or allowing these to pass through.

Figure 3:
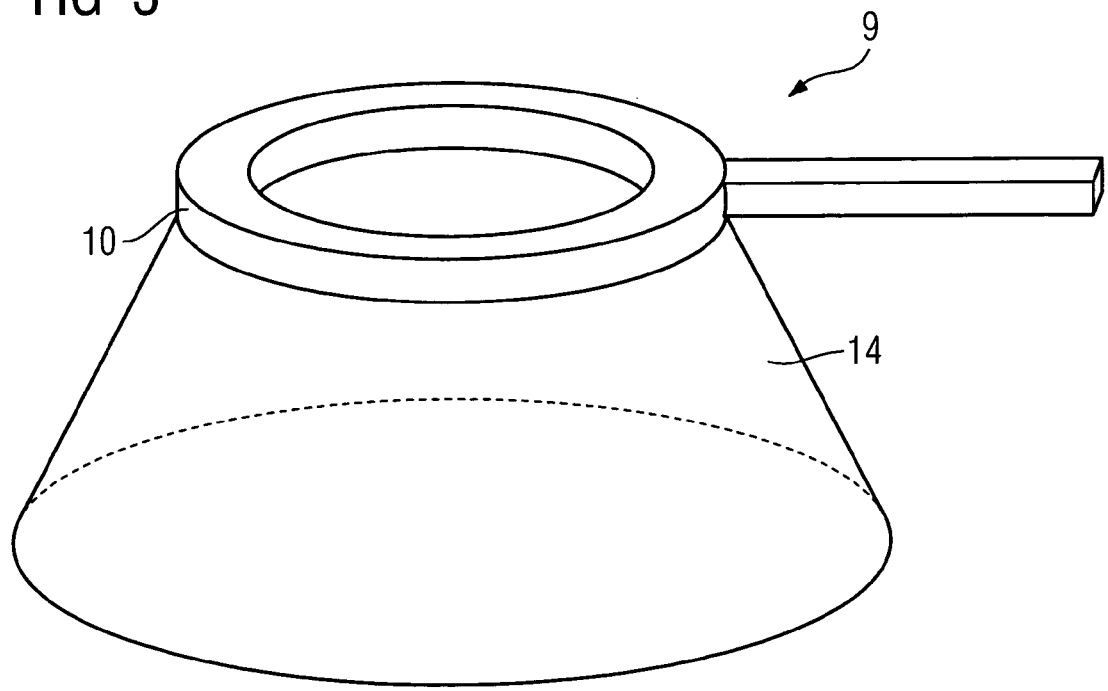
FIG. 3 a variant of the device according to the invention shown in FIG. 2.

FIG. 3 shows a variant of the device 9 shown in FIG. 2. The device 9 additionally has a light screen 14, which is cone-shaped in design and is affixed to the outer side of the ring 10. The light screen 14 may optionally be used and subsequently mounted on the device 9. The light screen 14 makes it possible to screen off existing light which comes in through windows, for example, or is caused by artificial lighting.

Figure 4:
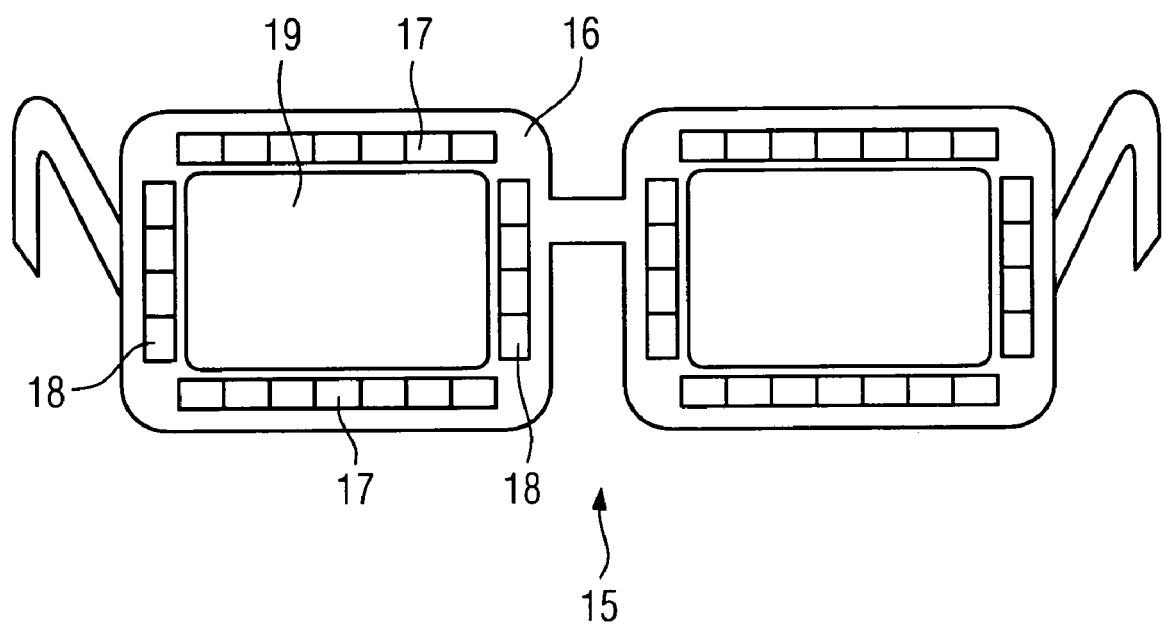
FIG. 4 a second embodiment of the device according to the invention.

FIG. 4 shows a further embodiment of the invention, configured as a pair of glasses 15. The frame 16 for the glasses 15 has a plurality of first selectable light sources 17 and likewise a plurality of second selectable light sources 18, configured as light-emitting diodes. The horizontally arranged light sources 17, when switched on, emit light at the excitation wavelength of the fluorescent dye. The vertically arranged light-emitting diodes of the light source 18, when switched on, illuminate the part of the body under investigation at a wavelength of about 600 nm. One or preferably both of the spectacle lenses 19 is or are configured as filters, to filter out unwanted components of the existing light. By means of a switching means, which is not shown, the light sources 17, 18 can be turned on and off alternately, with the result that the impression of a merged image is created for the user, as in the previous embodiment. The glasses 15 have the advantage that the user has both hands free to carry out an investigation or operation.

The wavelengths given for the fluorescent dye should not be seen as being restrictive. It is possible to use any fluorescent dyes which can be excited outside the existing light spectrum and the emission of which ensues at a wavelength that can be blocked out of the existing light.

The device is simple in design, can be manufactured economically and can be used for many investigations close to the surface. The device allows an investigation to be carried out in an optimum and simple manner.

The invention claimed is:

1. A device for making visible a pathological change in a part of a patient's body labeled with a fluorescent dye, comprising:
   a first switchable light source configured to emit light having a wavelength essentially matching an excitation wavelength of the fluorescent dye for triggering the emission of light having a wavelength essentially matching an emission wavelength of the fluorescent dye and for producing a first image;
   a second switchable light source configured to emit visible light having a wavelength different from the emission wavelength of the fluorescent dye for producing a second image;
   a switching device configured to create an impression of a merged image of the first and second images by alternately switching on and off the first and second switchable light sources at a frequency such that a human eye cannot differentiate between the first and second images; and
   a filter for filtering out components of ambient light having a wavelength essentially matching the emission wavelength, wherein the filter is configured to be switched on and off in sync with the second light source.

2. The device according to claim 1, wherein the filter includes adjustable filter parameters.

3. The device according to claim 2, wherein the filter parameters include a wavelength range to be filtered out.

4. The device according to claim 2, wherein the filter includes light-permeable glass through which the part of the patient's body can be viewed.

5. The device according to claim 1, wherein the switching device is configured to selectively switch on and off the first and second switchable light sources at an adjustable switching frequency.

6. The device according to claim 1, wherein the device is configured as a hand-held device.

7. The device according to claim 6, further comprising a handle.

8. The device according to claim 1, wherein the device is configured as a pair of glasses.

9. The device according to claim 8, wherein the pair of glasses includes at least one spectacle lens configured as a filter.

10. The device according to claim 1, further comprising a light screen for screening off ambient light.

11. The device according to claim 1, further comprising a wireless power supply.

12. The device according to claim 11, wherein the wireless power supply is an accumulator or a battery.

* * * * *